(12) United States Patent
Slivka et al.

(10) Patent No.: US 10,736,670 B2
(45) Date of Patent: Aug. 11, 2020

(54) SPINOUS PROCESS SPACER HAMMOCK

(71) Applicant: DePuy Synthes Products, Inc., Raynham, MA (US)

(72) Inventors: Michael Andrew Slivka, Taunton, MA (US); Michael J O'Neil, West Barnstable, MA (US); Hassan Serhan, South Easton, MA (US); Michael Fisher, Lawrenceville, GA (US); John Riley Hawkins, Cumberland, RI (US)

(73) Assignee: DePuy Synthes Products, Inc., Raynham, MA (US)

( * ) Notice: Subject to any disclaimer, the term of this patent is extended or adjusted under 35 U.S.C. 154(b) by 0 days.

(21) Appl. No.: 16/163,876

(22) Filed: Oct. 18, 2018

(65) Prior Publication Data
US 2019/0046246 A1 Feb. 14, 2019

Related U.S. Application Data

(63) Continuation of application No. 16/012,316, filed on Jun. 19, 2018, now abandoned, which is a continuation of application No. 15/648,804, filed on Jul. 13, 2017, now abandoned, which is a continuation of application No. 14/878,048, filed on Oct. 8, 2015, now Pat. No. 9,724,133, which is a continuation of application No. 11/770,802, filed on Jun. 29, 2007, now abandoned.

(51) Int. Cl.
*A61B 17/70* (2006.01)
*A61B 17/88* (2006.01)
*A61B 17/68* (2006.01)

(52) U.S. Cl.
CPC ...... *A61B 17/7068* (2013.01); *A61B 17/7053* (2013.01); *A61B 17/7062* (2013.01); *A61B 17/8869* (2013.01); *A61B 2017/681* (2013.01)

(58) Field of Classification Search
CPC ............ A61B 17/7053; A61B 17/7062; A61B 17/7068
See application file for complete search history.

(56) References Cited

U.S. PATENT DOCUMENTS

| | | | |
|---|---|---|---|
| 5,725,582 A | 3/1998 | Bevan | |
| 6,312,431 B1 * | 11/2001 | Asfora | A61B 17/7068 606/263 |
| 6,582,433 B2 | 6/2003 | Yun | |
| 6,706,070 B1 | 3/2004 | Wagner | |
| 6,761,720 B1 | 7/2004 | Senegas | |
| 2005/0203512 A1 | 9/2005 | Hawkins | |
| 2006/0064165 A1 | 3/2006 | Zucherman | |
| 2006/0085070 A1 | 4/2006 | Kim | |
| 2006/0122620 A1 | 6/2006 | Kim | |
| 2006/0217726 A1 * | 9/2006 | Maxy | A61B 17/7062 606/248 |
| 2007/0032790 A1 | 2/2007 | Aschmann | |
| 2007/0083200 A1 | 4/2007 | Gittings | |
| 2007/0270828 A1 | 11/2007 | Bruneau | |

* cited by examiner

*Primary Examiner* — Si Ming Ku

(57) ABSTRACT

A spinal distractor for distracting opposed vertebrae in which a pair of elements are threadably connected by a screw having opposing threads, wherein actuating the screw spreads the elements apart and pushes the vertebrae apart.

1 Claim, 7 Drawing Sheets

SPINOUS PROCESS SPACER HAMMOCK

CONTINUING DATA

This continuation application claims priority from co-pending U.S. patent application Ser. No. 16/012,316, entitled "Spinous Process Spacer Hammock", Slivka et al., filed Jun. 19, 2018, which claims priority from U.S. Ser. No. 15/648,804, entitled "Spinous Process Spacer Hammock", Slivka et al., filed Jul. 13, 2017, from U.S. patent application Ser. No. 14/878,048, entitled "Spinous Process Spacer Hammock", Slivka et al., filed Oct. 8, 2015, and from U.S. patent application Ser. No. 11/770,802, entitled "Spinous Process Spacer Hammock", Slivka et al., filed Jun. 29, 2007, the specifications of which are incorporated by reference in their entireties.

BACKGROUND OF THE INVENTION

Patients suffering from low back or leg pain frequently have stenosis of the vertebral and/or neural foramen that constricts their spine-related nerves. It has been shown that applying traction to the spinous processes may alleviate this pain and several devices have been developed that accomplish this. However, many of these devices are either difficult to implant, do not stay in place, or wear away the bone of the spinous process due to poor conformance of the device.

US Published Patent Application No. US20060122620 ("Kim I") discloses a posterior element distraction system for implantation at a spinal motion segment comprising a superior vertebra, an inferior vertebra, each vertebra comprising a posterior element comprising a spinous process, laminal portions and a set of facet joints, and further comprising an interspinous space between the spinous processes, the system comprising: at least one lateral member for positioning on a side of the spinal motion segment and outside the interspinous space, wherein the at least one lateral member has an unexpanded configuration and an expanded configuration; and first and second transverse members extending transversely from the at least one lateral member, wherein when the system is operatively implanted at a spinal motion segment and the at least one lateral member is in an expanded configuration, the transverse members are caused to contact a portion of either the superior or inferior posterior elements thereby providing distraction between the superior and inferior posterior elements.

US Published Patent Application No. US20060085070 (Kim II) discloses a device for stabilizing at least one spinal motion segment comprising a first vertebra having a first spinous process and a second vertebra having a second spinous process, the device comprising: an undeployed configuration having an axial dimension and a radial dimension substantially transverse to the axial dimension; and a deployed configuration having an axial dimension and a radial dimension substantially transverse to the axial dimension; wherein the radial dimension of the undeployed configuration is less than the radial dimension in the deployed configuration.

US Published Patent Application No. 2005-0203512 ("Hawkins") discloses an interspinous implant for insertion into an interspinous space between a first and second spinous process, the first spinous process having a first and second side, the implant comprising: a) a first base having a side surface adapted for fixation to a first side of the first spinous process, b) a second base having a side surface adapted for fixation to a second side of the first spinous process, c) a first flexible ligament having a first end connected to the first base and a second end connected to the second base.

U.S. Pat. No. 6,582,433 (Yun) discloses a device and method that immobilizes the vertebral bodies by immobilizing the respective spinous process extending therefrom. The device contains a spacer extending from a body with the spacer adapted to be positioned between adjacent spinous processes so that the spacer may be located close to the spine. A strap connected with the body is designed to engage the spinous processes, such that the device may be adjusted to be positioned about the spinous processes. The device ensures that the spacer remains positioned between adjacent spinous processes. The method to insert the device minimizes destruction to body tissue, thus it is less traumatic to the patient and allows for the patient to recover from the procedure faster than conventional methods.

It is an object of the present invention to provide an interspinous spacer that is easy to implant, remains in place after it is implanted, and whose excellent conformance to the adjacent spinous processes prevents wearing away of the adjacent spinous processes during use.

SUMMARY OF THE INVENTION

In a first embodiment of the present invention, there is provided an interspinous spacer that comprises a flexible strap or ligament that is threaded through two slotted plates positioned on either side of the spinous processes and a means for tensioning the strap and holding it in place once the desired distraction has been achieved. Distraction of the spinous processes is achieved by locating the slots on the straps such that the distance between the slots on each plate is larger than the distance between the spinous processes. Adjustable distraction of the spinous processes may also be achieved by varying the level of tension in the strap. Increasing the level of tension in the strap increases the distraction of the spinous processes (up to the distance between the upper and lower throughholes), while decreasing the level of tension decreases the distraction. In addition, as the ligament is tensioned, the two braces automatically become snugly opposedly positioned against the sides of the spinous processes, thereby helping to keep the device from migrating during use.

In another embodiment, the spacer comprises two straps or ligaments, one located at the cranial and one at the caudal portions of the device, with each strap being fixed to the respective inner surfaces of two plates positioned on opposing sides of the spinous processes. For this embodiment, there is preferably a centrally located distance adjustment element that connects the two plates and may be adjustable in a medial-lateral direction such that the adjustment changes the tension of the straps and thereby enables distraction of the spinous processes. In one preferred embodiment, the central distance adjustment element is a threaded rod and the plates have threaded holes for mating with the threaded rod. Preferably, the opposed holes are threaded in the opposite direction (right hand versus left hand threads) such that upon turning the threaded rod, the plates will move either away from each other or towards each other, thus either tightening or loosening the strap.

DETAILED DESCRIPTION OF THE INVENTION

Figure 1:
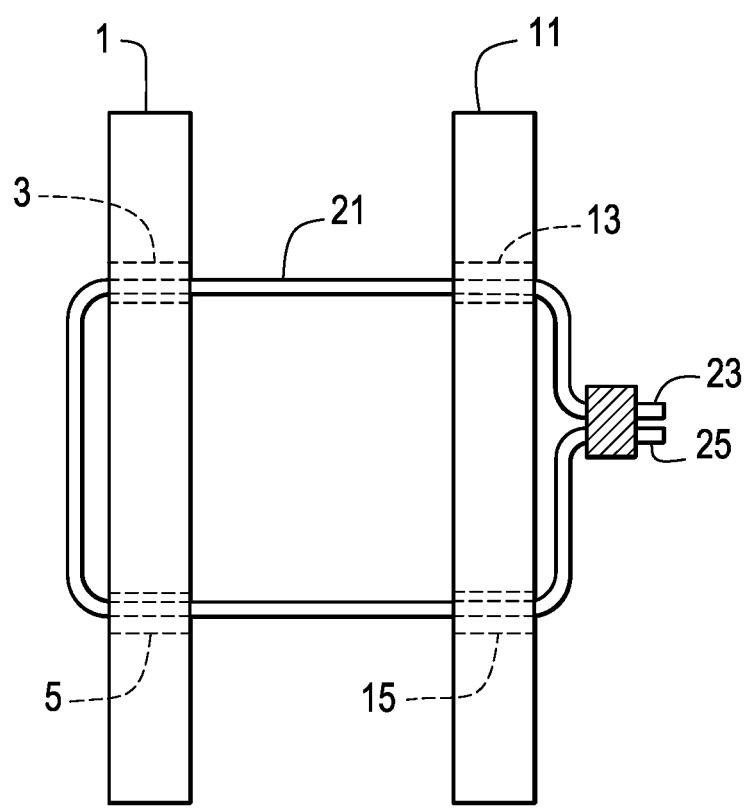
FIG. 1 discloses a first embodiment of the interspinous spacer of the present invention.

Now referring to FIG. 1, there is provided an interspinous spacer comprising:

a) a first brace 1 having an upper throughhole 3 and a lower throughhole 5, b) a second brace 11 having an upper throughhole 13 and a lower throughhole 15, c) a ligament 21 having a first end 23 and a second end 25, wherein the ligament extends from the upper throughhole of the first brace through the upper throughhole of the second brace, then through the lower throughhole of the second brace, then through the lower throughhole of the first brace, and
wherein the first end of the ligament is in mechanical connection with the second end of the ligament between the upper throughhole and a lower throughhole of the first brace.

Now referring to FIGS. 2a-2f, the spacer is assembled in situ as follows: First, and now referring to FIG. 2a, the ligament is drawn through each of the upper and lower holes of a first brace, with each end of the ligament exiting the respective holes in the same direction. Next, and now referring to FIG. 2b, the ligament and brace combination is inserted on a first side of the spine, is passed through the space between adjacent spinous processes SP and exits on the second side of the spine. The first brace is then oriented so that the portion of the ligament that runs between the holes of the first brace is located on the outer face 7 of the first brace, while the inner face 9 abuts the spinous processes.

Next, if needed, each end of the ligament is passed back through the space between the adjacent interspinous processes and extended back into the first half of the spine.

Figure 2A:
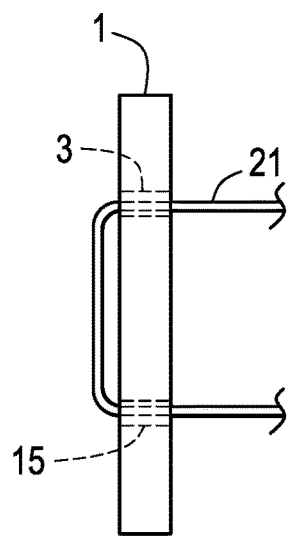
FIGS. 2a-2f disclose a method of implanting the spacer of FIG. 1.
Figure 2B:
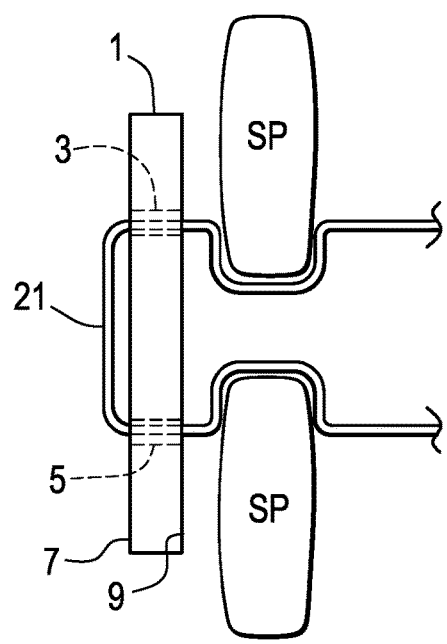
Figure 2C:
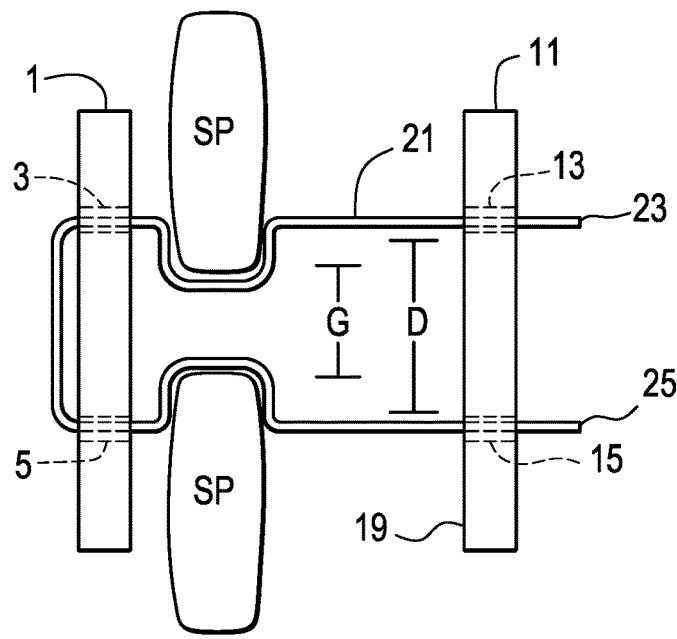

Next, and now referring to FIG. 2c, one end of the ligament is passed through the upper throughhole of the second brace, while the second end of the ligament is passed through the lower throughhole of the second brace. Each end of the ligament enters its respective throughhole from the same inner face 19 of the second brace.

Figure 2D:
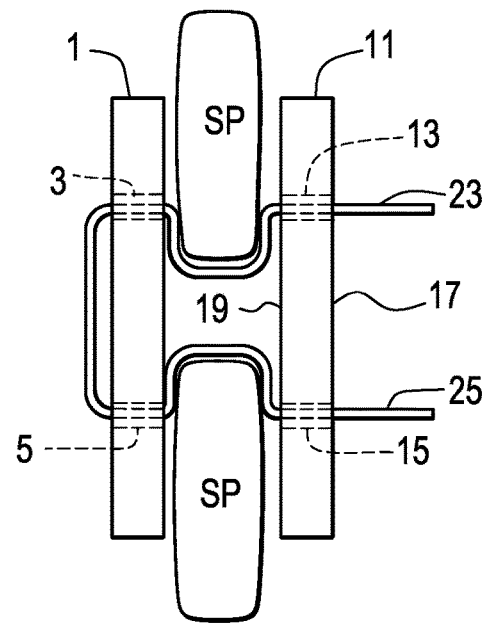

Next, and now referring to FIG. 2d, the second brace is then inserted into the first half of the spine and oriented so that its inner face 19 abuts the spinous processes, and the ends of the ligament are closer to the outer face 17 of the second brace.

Figure 2E:
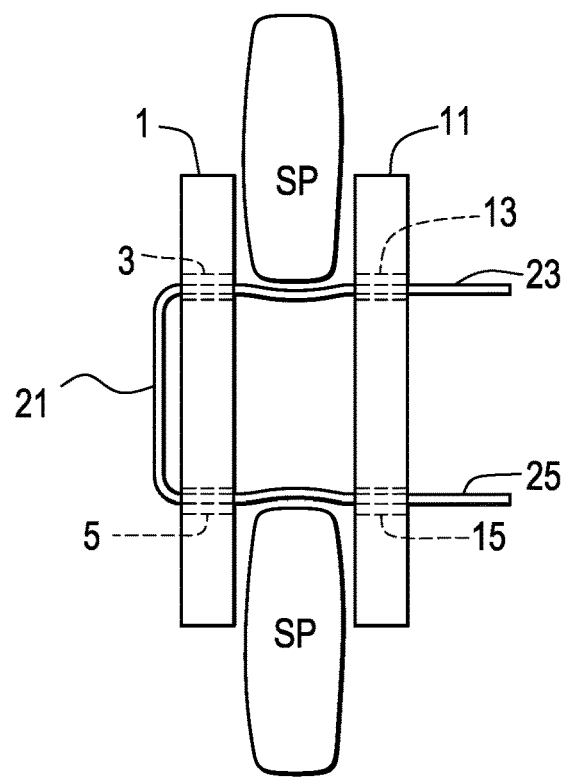

Next, and now referring to FIG. 2e, the respective end portions of the ligament are then pulled in unison so as to create tension in the ligament and thereby cause distraction of the upper and lower spinous processes. Since the distance D between the upper and lower slots on each plate (shown in FIG. 2c) is larger than the gap G between the spinous processes (shown in FIG. 2c), distraction is achieved when the ligament is tensioned.

Figure 2F:
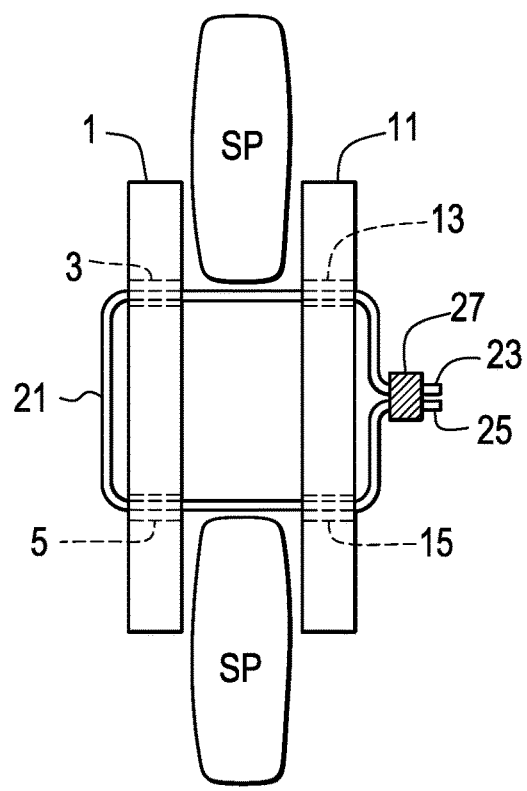

Lastly, and now referring to FIG. 2f, the respective end portions of the ligament are then mechanically connected by a connection means 27 (such as a crimpable tube) to make a permanent and continuous loop that extends through each of the upper and lower throughholes of each brace.

Therefore, in accordance with the present invention, there is provided a method of implanting an interspinous implant, comprising the steps of:

a) implanting a first brace having an upper throughhole and a lower throughhole on a first side of a spinous process, b) implanting a second brace having an upper throughhole and a lower throughhole on a second side of the spinous process, c) passing a ligament from the upper throughhole of the first brace through the upper throughhole of the second brace, d) passing the ligament from the upper throughhole of the second brace through the lower throughhole of the second brace, e) passing the ligament from the lower throughhole of the second brace through the lower throughhole of the first brace, and f) mechanically connecting a first end of the ligament with a second end of the ligament between the upper throughhole and a lower throughhole of the first brace.

In some embodiments, the first brace is implanted through a first incision on the first side of the spinous process, and the second first brace is implanted through the first incision. In some embodiments, the first brace is implanted through a first incision on the first side of the spinous process, and the second first brace is implanted through a second incision on the second side of the spinous process.

In one preferred embodiment, the means for tensioning the strap comprises a wheel around which the strap can wind as the wheel is turned, thus creating the tension in the strap. The wheel may be either a part of the implant or a part of an instrument.

Once the desired distraction is achieved, the position may be locked in place either by locking the wheel (in the case where the wheel is part of the implant) or by securing a blocking member on the strap. One such blocking member could be a metallic sleeve that is crimped into place, or a hardenable polymer formed in place. In some embodiments, the strap may be crimped and then glued in place. In other embodiments, the strap may be tied and then glued in place.

Figure 3:
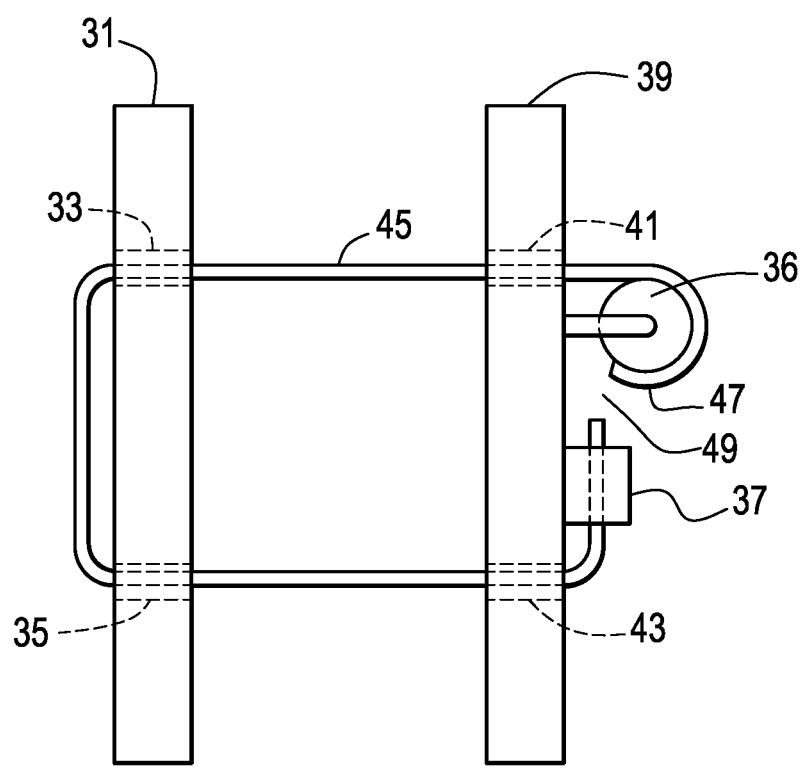
FIG. 3 discloses a preferred first embodiment of the interspinous spacer of the present invention.

Now referring to FIG. 3, there is provided an interspinous spacer comprising:

a) a first brace 31 having an upper throughhole 33, a lower throughhole 34, an intermediate section 35, and a wheel 36 and a crimpable tube 37 each mechanically connected to the intermediate section b) a second brace 39 having an upper throughhole 41 and a lower throughhole 43, c) a ligament 45 having a first end 47 and a second end 49, wherein the ligament extends from the wheel through upper throughhole of the first brace, through the upper throughhole of the second brace, then through the lower throughhole of the second brace, then through the lower throughhole of the first brace, and into the crimpable tube.

Figure 4:
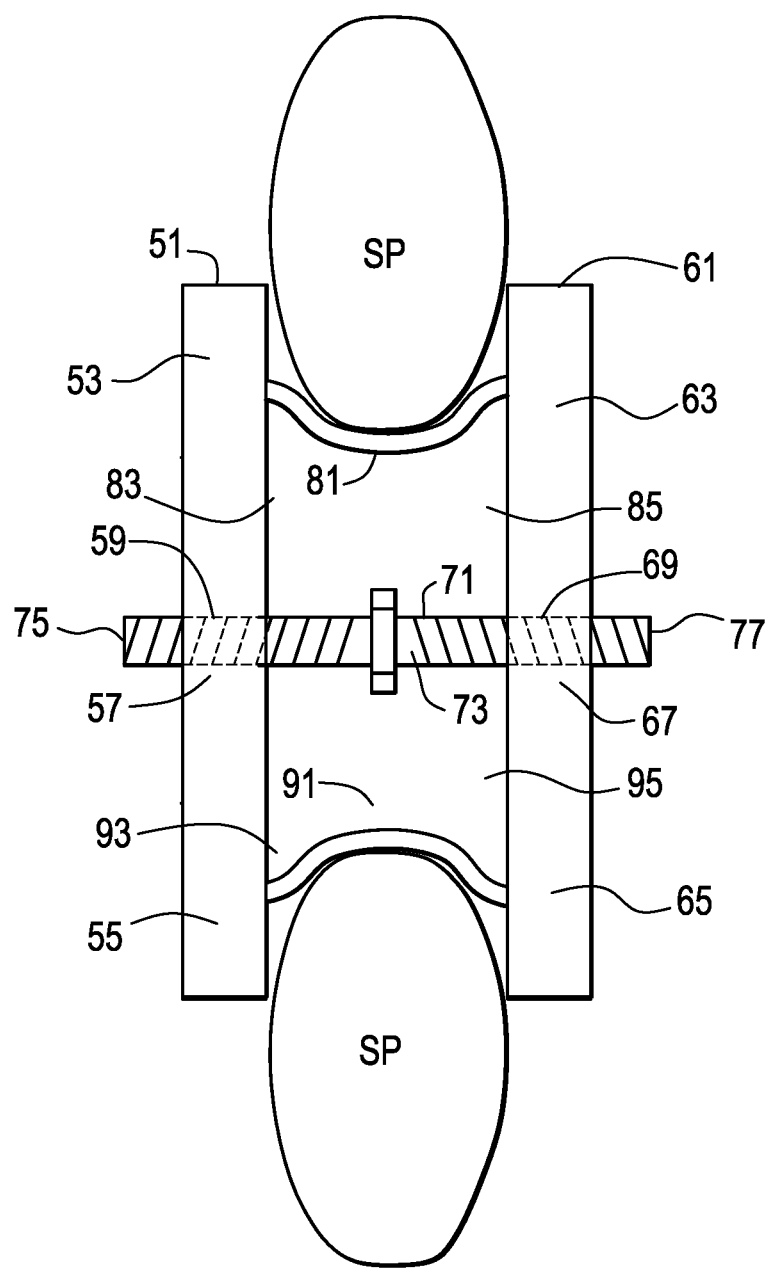
FIG. 4 discloses a second embodiment of the interspinous spacer of the present invention.

Now referring to FIG. 4, there is provided an interspinous spacer comprising:

a) a first brace 51 having an upper end portion 53, a lower end portion 55, and an intermediate portion 57, b) a second brace 61 having an upper end portion 63, a lower end portion 65 and an intermediate portion 67, c) a distance adjustment element 71 connected to each of the intermediate portions, d) an upper ligament 81 having a first end 83 and a second end 85, e) a lower ligament 91 having a first end 93 and a second end 95, wherein the upper ligament connects the upper end portion of the first brace to the upper end portion of the second brace, and wherein the lower ligament connects the lower end portion of the first brace to the lower end portion of the second brace.

Preferably, the distance adjustment element comprises a threaded rod 73 having a first end 75 threaded in one direction and a second end 77 threaded in a second direction, and the intermediate portion of each brace has a threaded hole 59, 69 adapted for threaded mating with the threaded rod. More preferably, a first threaded hole is threaded in a first direction while a second threaded hole is threaded in a second opposite direction.

In use, the device of FIG. 4 is implanted so that the first brace is located on a first side of the spinous processes, the second brace is located on a second side of the spinous processes, and the distance adjustment element is located in the gap between the spinous processes. The distance adjustment element is then actuated to decrease the distance between the braces. As the distance between the braces decreases, the two braces automatically become snugly opposedly positioned against the spinous processes, thereby helping to keep the device from migrating during use. As the distance increases, the two ligaments automatically become tensioned and press against the inner portion of the spinous processes, thereby causing distraction.

Preferably, when the strap or ligament contacts the spinous process, it is relatively wide in the anterior-posterior direction to maximize contact with the spinous processes, thus minimizing stress risers and thereby the potential wear of the strap or the bone. Thus, the strap preferably has a cross-section having a height and a width, wherein the width is greater than the height. Additionally, a protective guard may be placed over the contacting portions of the spinous processes in order to minimize this wear. Alternatively, a protective sleeve may be placed over the strap in the region where it interfaces with the bone. Also, the strap is preferably constructed of a wear-resistant material such as ultra-high molecular weight polyethylene. Other biocompatible materials may be used as well, including polyethylene terephthalate, polyetheretherketone (PEEK), polyurethane, or bioabsorbable materials such as poly(L-lactic acid), poly (glycolic acid) and other biocompatible materials known in the art. The strap may be constructed by weaving, braiding or knitting fibers or fiber bundles into a typical fabric form. In one preferred embodiment, a three-dimensional weaving pattern is used to create a thin and wide strap.

In some embodiments, more than one strap may be used. The straps may also be made of metal or elastormeric. They can be rigid or flexible. They can be made of a fabric or non-fabric material. They may comprise a belt, a weave, a composite or a laminate.

Some embodiments of the present invention may comprises a belted strap. An alternative embodiment to a woven or braided fabric ligament would be a composite or homogeneous belt of material. Similar to an automotive belt that uses grooves or ribs of material to help transfer load, the belted strap could use composite internal materials, potting compounds, or external surface features to enhance system performance. For example, a composite belted ligament could have a layer of steel or Kevlar™ material that would help to prevent material creep. Similarly, surface features on the belt could articulate with the spinous processes to prevent device migration or assist device placement.

As noted above, the device of the present invention may comprise multiple ligaments. There are many benefits to having multiple ligaments in the device of the present invention. One ligament with a cross-sectional width that is significantly larger in dimension than its cross-sectional thickness constrains the width of the ligament relative to the side plate width. For a plate where the ligament passes through a through-hole, the plate must be wider than the ligament unless it is acceptable to compress or fold the ligament where it passes through the plate. Another benefit to incorporating a plurality of ligaments between the side plates is redundancy. If one ligament within the plurality fails, the other ligaments can assume the load. Multiple ligaments can travel multiple pathways from one side plate to the other side plate—much like a traditional hammock. This splay of ligaments can enable the mechanical load to be spread over a larger area of the spinous process. A splay of ligaments may also allow for differential tightening between the ligaments. Differential tightening can be used to preferentially load bone at different regions of the spinous process. For example, three ligaments could be applied where the majority of the load is carried on the first and last ligaments and the middle ligament is only used in a modest capacity. Some degree of bone resorption and ligament settling can be expected. The first and third ligaments would create slight depressions in the local bone due to overload and subsequent Wolff's Law remodeling. This overload would be resolved by the second central ligament assuming more load during the settling. A positive consequence of this arrangement is that the device is now positively fixed in place between the spinous processes due to the remodeled bone depressions that prevent device migration. A multiplicity of ligaments might also mitigate the consequences of this situation by "over-loading" some ligaments with the expectation that they will cause bone resorption while the other ligaments osseo-integrate and assume a more "natural" load bearing status. Multiple smaller ligaments of material are easier to handle from a surgical perspective than one large strap or belt of material. Smaller ligaments would be more akin to traditional sutures. Multiple ligaments can be tied-off like sutures, and systems for fixing the ultimate length of these small ligaments is, again, more akin to the systems used to fix the length of traditional braided suture materials.

The plates are preferably constructed of biocompatible, wear-resistant materials known in the art such as titanium, stainless steel, PEEK, or carbon fiber-reinforced PEEK. The plates may be constructed such that they provide some flexibility once implanted—by either using more flexible materials such as PEEK, or making the plates sufficiently thin to allow for some flexing. For embodiments where the strap threads through the plates, the slots or holes in the plate preferably have rounded edges to prevent wear of the strap on the plate.

In preferred embodiments, each plate is manufactured from a material that possesses the desirable strength and stiffness characteristics for use as an interspinous spacer. The plates of the present invention may be made from any non-resorbable material appropriate for human surgical implantation, including but not limited to, surgically appropriate metals, and non-metallic materials, such as carbon fiber composites, polymers and ceramics.

The plates can be made of any structural biocompatible material including non-resorbable polymers (CFRP, PEEK, UHMWPE), resorbables (such as PLA, PLGA, PGA), metallics (SS, Ti-6Al-4V, CoCr,) and ceramics. The plate material is preferably selected from the group consisting of metal and composite (such as PEEK/carbon fiber).

If a metal is chosen as the material of construction for a component, then the metal is preferably selected from the group consisting of titanium, titanium alloys (such as Ti-6Al-4V), chrome alloys (such as CrCo or Cr—Co—Mo) and stainless steel.

The plate component may have teeth; porous beaded surfaces to encourage bony ingrowth; or fixation features on the ingrowth surfaces to prevent device migration.

If a polymer is chosen as a material of construction for a component, then the polymer is preferably selected from the group consisting of polyesters, (particularly aromatic esters such as polyalkylene terephthalates, polyamides; polyalkenes; poly(vinyl fluoride); PTFE; polyarylethyl ketone PAEK; and mixtures thereof.

If a ceramic is chosen as a material of construction for a component, then the ceramic is preferably selected from the group consisting of alumina, zirconia and mixtures thereof. It is preferred to select an alumina-zirconia ceramic, such as BIOLOX Delta™, available from CeramTec of Plochingen, Germany.

In some embodiments, the first plate consists essentially of a metallic material, preferably a titanium alloy or a chrome-cobalt alloy. In some embodiments, the second plate consists essentially of the same metallic material as the first plate.

In some embodiments, the components are made of a stainless steel alloy, preferably BioDur® CCM Plus® Alloy available from Carpenter Specialty Alloys, Carpenter Technology Corporation of Wyomissing, Pa.

The plates may be rigid or flexible.

In some embodiments, the plates are made from a composite comprising carbon fiber. Composites comprising carbon fiber are advantageous in that they typically have a strength and stiffness that is superior to neat polymer materials such as a polyarylethyl ketone PAEK.

In some embodiments, each plate is made from a polymer composite such as a PEKK-carbon fiber composite.

Preferably, the composite comprising carbon fiber further comprises a polymer. Preferably, the polymer is a polyarylethyl ketone (PAEK) or polyphenylene. More preferably, the PAEK is selected from the group consisting of polyetherether ketone (PEEK), polyether ketone ketone (PEKK) and polyether ketone (PEK). In preferred embodiments, the PAEK is PEEK.

In some embodiments, the carbon fiber comprises between 1 vol % and 60 vol % (more preferably, between 10 vol % and 50 vol %) of the composite. In some embodiments, the polymer and carbon fibers are homogeneously mixed. In others, the material is a laminate. In some embodiments, the carbon fiber is present in a chopped state. Preferably, the chopped carbon fibers have a median length of between 1 mm and 12 mm, more preferably between 4.5 mm and 7.5 mm. In some embodiments, the carbon fiber is present as continuous strands.

In especially preferred embodiments, the composite comprises:
a) 40-99% (more preferably, 60-80 vol %) polyarylethyl ketone (PAEK), and
b) 1-60% (more preferably, 20-40 vol %) carbon fiber, wherein the polyarylethyl ketone (PAEK) is selected from the group consisting of polyetherether ketone (PEEK), polyether ketone ketone (PEKK) and polyether ketone (PEK).

In some embodiments, the composite consists essentially of PAEK and carbon fiber. More preferably, the composite comprises 60-80 wt % PAEK and 20-40 wt % carbon fiber. Still more preferably, the composite comprises 65-75 wt % PAEK and 25-35 wt % carbon fiber.

In some embodiments, the holes of the plates may be replaced by positive features such as rungs, that can help anchor the ligament.

Figure 5:
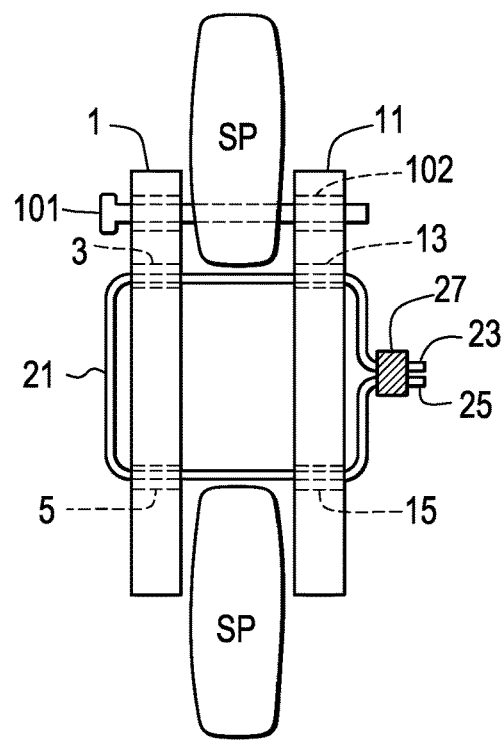
FIG. 5 discloses an embodiment of the present invention having a transverse bolt.
Figure 6:
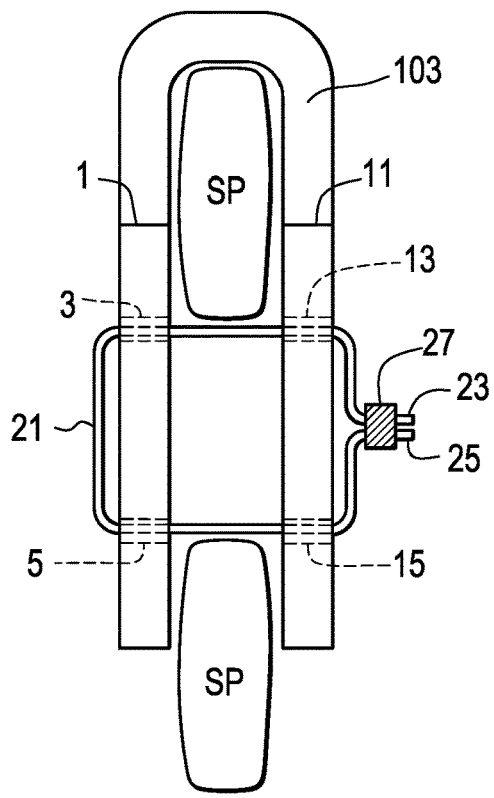
FIG. 6 discloses an embodiment of the present invention having a prosthetic ligament connecting to each plate and extending up and over the upper spinous process.
Figure 7:
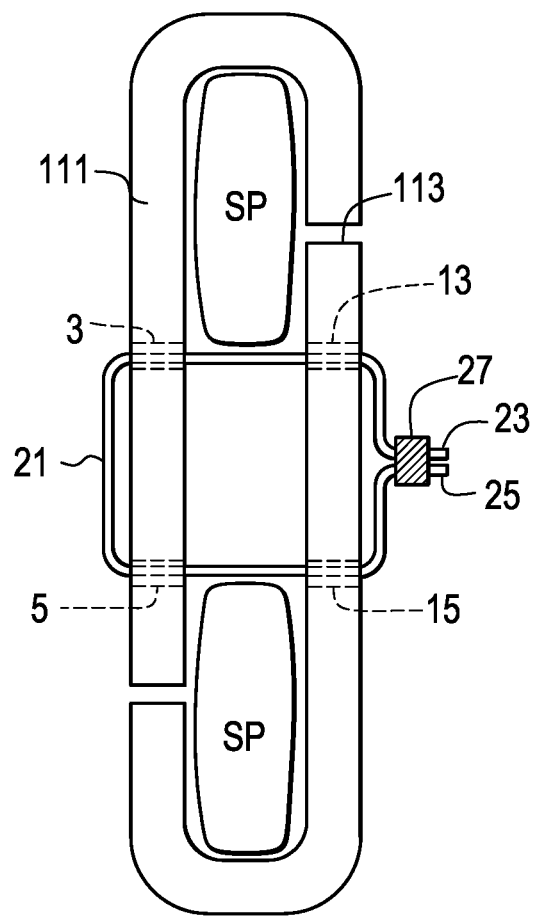
FIG. 7 discloses an embodiment of the present invention having two J-shaped plates.

In some embodiments, the device of the present invention contains extra features that insure that the device stays in place when set against the spinous processes. FIG. 5 discloses an embodiment of the present invention having a transverse bolt 101 extending through a throughhole 102 in each of the plates. FIG. 6 discloses an embodiment of the present invention having a prosthetic ligament 103 connected to each plate and extending up and over the upper spinous process. FIG. 7 discloses an embodiment of the present invention having two J-shaped plates 111, 113 that encircle the spinous processes.

Figure 8:
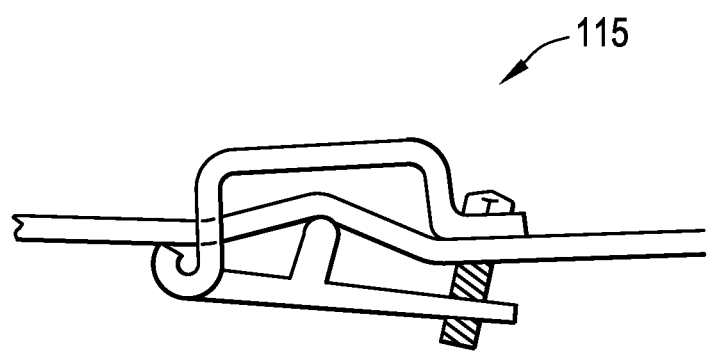
FIG. 8 discloses a crimp block revision tool of the present invention.

FIG. 8 discloses a crimp block revision tool 115 of the present invention. Generally, the device's ligament is permanently fixed at a certain length intraoperatively. However, it is expected that a situation may present in some patients postoperatively that requires further shortening of the ligament. To address this need to post-operatively shorten an implanted ligament, an implantable crimp block 115 is provided that captures a greater amount of ligament material between two points than is represented by the linear distance between those points. For example, the ligament material must travel a tortuous pathway between the two points such that the length of tether material between the points is greater than the fixed linear distance between the points. In the embodiment of FIG. 8, two hinged plates with stand-offs of height A placed along the length of the plate at a distance 2B are closed around a ligament of material. The stand-offs nest together, thereby creating a tortuous pathway for the intervening ligament material. For a plate with one central stand-off of height A that nests between two stand-offs placed at the ends of the other plate of length 2B (total crimp block length of 2B), the amount of ligament material captured between these stand-offs is $2*(A^2+B^2)^{1/2}>2*B$. Additional stand-offs can be added. Thus, the reduction in ligament length for a crimp block containing N stand-off segments of height A with distance 2*B between the stand-offs is characterized as $\Delta l = N*2*[(A^2+B^2)^{1/2}-B]$.

Preferably, the device of the present invention is placed between the spinous processes using a minimally invasive approach that spares the supraspinous ligament. For the first embodiment described above having a continuous ligament, the first plate with the strap woven through is threaded through the muscle, bone and ligamentous structures from the contralateral side, followed by threading of the second plate with the strap woven through to the ipsilateral side. The tensioning and position locking can then be accomplished through the same insertion approach used to place the plates. Thus, the entire procedure can be accomplished using a percutaneous technique.

Preferably, the device of the present invention is used in patients who have stenosis of the vertebral and/or neural foramen that constricts their spine-related nerves and thereby suffer from low back or leg pain.

We claim:

1. An interspinous spacer comprising:
   a) a first brace having an upper throughhole and a lower throughhole,
   b) a second brace having an upper throughhole and a lower throughhole,
   c) a single strap having a first end and a second end, wherein a first portion of the strap is located between the upper throughhole of the first brace and the upper throughhole of the second brace, wherein a second portion of the strap is located between the lower throughhole of the first brace and the lower throughhole of the second brace, wherein a distance D between the upper and lower througholes on each brace is larger than a smallest distance between the first strap portion and the second strap portion, and wherein no portion of the strap passes through bone.

* * * * *